United States Patent [19]

Ávár

[11] Patent Number: 4,876,299
[45] Date of Patent: Oct. 24, 1989

[54] OXALANILIDES USEFUL AS U.V. ABSORBERS

[75] Inventor: Lajos Ávár, Biel-Benken, Switzerland

[73] Assignee: Sandoz Ltd., Basel, Switzerland

[21] Appl. No.: 32,672

[22] Filed: Apr. 1, 1987

[30] Foreign Application Priority Data

Apr. 4, 1986 [GB] United Kingdom ............... 8608315

[51] Int. Cl.$^4$ ............... C07D 211/56; C07C 103/147; C08K 5/34; C08K 5/20
[52] U.S. Cl. ........................... 524/99; 564/152; 564/153; 564/190; 564/224; 524/102; 524/217; 524/219
[58] Field of Search ............... 564/152, 153; 546/190, 546/224; 524/99

[56] References Cited

U.S. PATENT DOCUMENTS 3,529,982 9/1970 Luethi et al. ............... 564/153
3,542,573 11/1970 Biland et al. ............... 564/153
3,906,041 9/1975 Hofer et al. ............... 564/153
4,730,017 3/1988 Avar ............... 546/190

OTHER PUBLICATIONS

Mar. "Advanced Organic Chemistry" (McGraw-Hill)(1985) pp. 342-343.

Primary Examiner—Robert T. Bond
Attorney, Agent, or Firm—Gerald D. Sharkin; Richard E. Vila; Thomas C. Doyle

[57] ABSTRACT

A compound of formula I

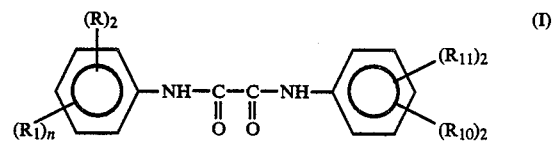

in which R, $R_1$, $R_{10}$ and $R_{11}$ are organic radicals. These compounds are suitable as U.V. absorbers.

13 Claims, No Drawings

OXALANILIDES USEFUL AS U.V. ABSORBERS

The invention relates to oxalanilide derivatives that are useful as U.V. absorbers in polymeric material.

According to the invention there is provided a compound of formula I

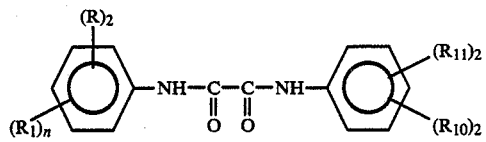
(I)

in which each R independently, is hydrogen, $C_{1-8}$alkyl, $C_{1-8}$alkoxy or halogen or both groups R are attached to carbon atoms in a position ortho to one another and together with the carbon atoms to which they are attached form a carbocyclic or heterocyclic group; n is 1 or 2;

$R_1$ is $-OCH_2-CO-X-R_4$ where X is $-O-$ or $-N(R_3)-$;

$R_4$ is linear or branched $C_{1-22}$alkyl, $C_{5-6}$cycloalkyl or

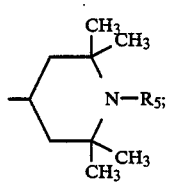

$R_3$ is hydrogen or $C_{1-4}$alkyl;

$R_5$ is hydrogen, oxygen, $C_{1-8}$alkyl or $-CO-R_6$;

$R_6$ is $C_{1-6}$alkyl, phenyl, $-CO-OC_{1-4}$alkyl or $-NR_7R_8$;

$R_7$ is hydrogen, $C_{1-12}$alkyl; $C_{5-6}$cycloalkyl, phenyl or $C_{1-12}$alkyl phenyl;

$R_8$ is hydrogen or $C_{1-12}$alkyl;

each $R_{10}$, independently, is selected from hydrogen, halogen $C_{1-4}$alkyl, $C_{2-4}$alkenyl, $C_{1-8}$-alkoxy, phenoxy, phenyl, phenyl$C_{1-4}$alkyl or $C_{1-4}$alkyl phenyl; and each $R_{11}$ independently has a significance of $R_{10}$ or $R_1$, independently of $R_{10}$ or $R_1$;

or both groups $R_{11}$ are hydrogen and both groups $R_{10}$ are attached to carbon atoms ortho to one another and together with the carbon atoms to which they are attached form a carbocyclic or heterocyclic group. In such a case, preferably both groups $R_{10}$ together with the phenyl group to which they are attached form a 9 or 10 carboxyclic or heterocyclic group, more preferably a group of formula α or β

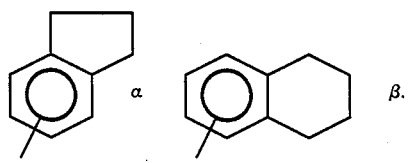

For the avoidance of doubt in this Specification, where a symbol appears more than once in a formula its significances are independent of one another unless indicated to the contrary. In this Specification $C_{1-8}$alkyl is preferaly $C_{1-4}$alkyl, $C_{1-4}$alkyl is preferably methyl or ethyl, $C_{1-4}$alkoxy is preferably methoxy or ethoxy and halogen is preferably chloro or bromo unless indicated to the contrary.

Preferably n is 1.

Preferably R is R' where R' is hydrogen or $C_{1-4}$alkoxy.

Preferably $R_1$ is $R_1'$ where $R_1'$ is $-O-CH_2COOR_4'$, more preferably $R_1$ is $R_1''$ where $R_1''$ is $-O-CH_2COOR_4''$, most preferably $R_1$ is $R_1'''$ where $R_1'''$ is $-O-CH_2COOR_4'''$ where $R_4'$, $R_4''$ and $R_4'''$ are as defined below.

Preferably when both groups R form a heterocyclic or carbocyclic group, both groups R together with the phenyl group to which they are attached form a 9 or 10 membered group, more preferably a group of formula α or β as defined above.

Preferably at least one $R_1$ (or $R_1'$) and/or $R_{11}$ (or $R_{11}'$) is ortho to the $-NH-$group on the same phenyl ring in the oxanilides of formula I.

Preferably $R_3$ is $R_3'$ where $R_3'$ is hydrogen or methyl, more preferably hydrogen.

Where $R_4$ is a $C_5$ or $C_6$ cycloalkyl, preferably $R_4$ is cyclohexyl.

Preferably $R_4$ is $R_4'$ where $R_4'$ is linear or branched $C_{1-12}$alkyl or N-unsubstituted, N-methyl or N-acetyl 2,2,6,6-tetramethyl piperidine; more preferably $R_4''$ where $R_4''$ is linear or branched $C_{1-8}$alkyl or N-substituted, N-methyl or N-acetyl 2,2,6,6-tetramethyl piperidine; most preferably $R_4'''$ where $R_4'''$ is iso-$C_{3-8}$alkyl (especially $-CH_2-CH(C_{1-2}alkyl)[(CH_2)_{1-3}CH_2)]_{n-1}H$ or N-unsubstituted 2,2,6,6-tetramethyl piperidine, where n is 1 or 2.

Preferably $R_5$ is $R_5'$ where $R_5'$ is hydrogen or $C_{1-4}$alkyl or $-CO-C_{1-4}$alkyl.

Preferably $R_{10}$ is $R_{10}'$ where $R_{10}'$ is hydrogen, chloro, $C_{1-4}$alkyl, $C_{1-4}$alkoxy, phenyl or phenoxy. More preferably $R_{10}$ is $R_{10}''$ where $R_{10}''$ is hydrogen or $C_{1-4}$alkoxy.

Preferably $R_{11}$ is $R_{11}'$ where $R_{11}'$ is $R_1'$ or $R_{10}''$, independently of $R_1'$ or $R_{10}'$; more preferably $R_{11}$ is $R_{11}''$ where $R_{11}''$ is a significance of $R_1'$ independently of $R_1'$.

Preferably X is oxygen.

One group of preferred compounds of formula I are of formula II

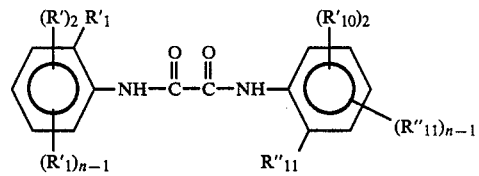
(II)

in which n, R', $R_1'$, $R_{10}'$ and $R_{11}''$ are as defined above. Preferably in the compound of formula II n=1.

Preferably the compounds of formula II are symmetrical.

Another group of preferred compounds are asymmetric compounds of formula III

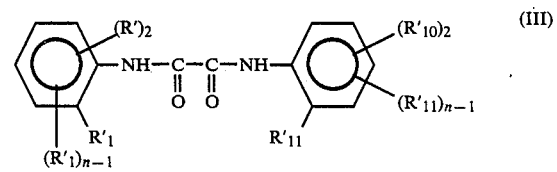
(III)

in which R', $R_1'$, n, $R_{10}'$ and $R_{11}'$ are as defined above. Preferably in the compound of formula III n=1.

Compounds of formula I can be prepared by reacting one mole of a compound of formula IV

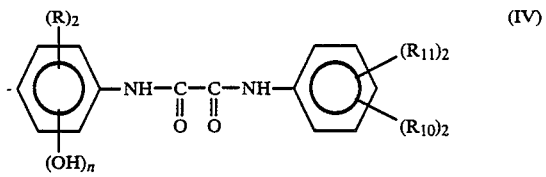

with n moles of a compound of formula V

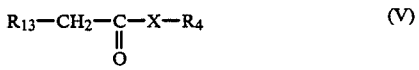

where $R_{13}$ is halogen and the other symbols are as defined above.

Preferably the reaction of a compound of formula IV with a compound of formula V can be carried out at a temperature of 20° to 200° C., more preferably 40°–110° C. Preferably the reaction is carried out in alkaline medium, more preferably at a pH of 8–13, most preferably at a pH of 9–12.

Compounds of formula IV and V are known or may be prepared by known methods from known compounds.

Further, according to the invention there is provided a composition comprising a polymeric material and a compound of formula I defined above.

Preferably a composition according to the invention is a lacquer composition in which the polymeric material is an acrylic alkyd or polyester resin. Such lacquer compositions can be metallic one or two layer lacquer compositions or one or two layer uni-lacquer compositions.

Preferably a lacquer composition according to the invention is a stoving lacquer composition.

Compounds of formula I are useful as stabilizers to protect polymeric materials against degradation by light. The compounds have particularly good solubility and miscibility in solvent systems and in liquid polymers as well as in prepolymers, which makes them useable in a wide range of polymeric materials.

The concentration of compound of formula I employed in the polymeric material is suitably 0.01 to 5% by weight, preferably 0.02 to 1% by weight. The compound may be added before, during or after the polymerization step, and may be added in solid form; in solution, preferably as a liquid concentrate containing from 20 to 80% by weight of compound of formula I; or as a solid masterbatch composition containing 20 to 80% by weight of compound of formula I and 80 to 20% by weight of a solid polymeric material which is identical with or compatible with the polymeric material to be stabilized.

Suitable polymeric materials include plastic materials for example polyethylene, polypropylene, ethylene/propylene copolymers, polyvinyl chloride, polyester, polyamide, polyurethane, polyacrylonitrile, ABS, terpolymers of acrylates, styrene and acrylonitrile, styrene/acrylonitrile and styrene/butadiene. Other plastics materials such as polybutylene, polystyrene, chlorinated polyethylene, polycarbonate, polymethylmethacrylate, polyphenylene oxide, polypropylene oxide, polyacetals, phenol/formaldehyde resins and epoxy resins may also be used. Preferred plastic materials are polypropylene, polyethylene, ethylene/propylene co-polymers and ABS. Natural polymers for example natural rubber may also be stabilized, as may lubricating oils containing polymeric material.

The compounds of formula I may be incorporated by known methods into the polymeric material to be stabilized. Of particular importance is blending of the compounds with thermoplastic polymers in the melt, for example in a melt blender or during the formation of shaped articles, including foils, films, tubes, containers, bottles, fibres and foams by extrusion, injection moulding, blow moulding, spinning or wire coating.

The compounds of formula I can also be used for light stabilising polyamide fibres.

It is not essential for the polymeric material to be fully polymerised before mixing with the compounds according to the invention. The compounds may be mixed with monomer, prepolymer or precondensate, and the polymerisation or condensation reaction carried out subsequently. This will of course be the preferred method of incorporation of the compound into thermosetting polymers which cannot be melt blended.

Compounds of formula I can be used alone or as aqueous dispersions especially in water-borne systems or in combination with other light stabilisers for example U.V. stabilisers. Examples of U.V. stabilisers are hindered amine light stabilisers such as N-unsubstituted or N-substituted (e.g. alkyl or acyl)-2,2,6,6-tetraalkylpiperidine compounds (in particular the 2,2,6,6-tetramethylpiperidine compounds). Such a combination may give a synergistic effect.

The compounds of formula I may be used alone or in combination with other stabilizers, for example antioxidants. Examples include sterically hindered phenols, sulphur or phosphorus-containing compounds or mixtures of these. Examples are benzofuran-2-ones; indolin-2-ones and sterically hindered phenols such as beta(4-hydroxy-3,5-ditert.-butylphenyl)-propionyl stearate, methane tetrakis-(methylene-3(3′,5′-ditert.-butyl-4-hydroxyphenyl-)-propionate, 1,1,3-tris-(2-methyl-4-hydroxy-5-tert.-butylphenyl)-butane, 1,3,5-tris(4-tert.-butyl-3-hydroxy-2,6-di-methylbenzyl)-1,3,5-triazin-2,5,6(1H, 3H, 5H)-trione, bis-(4-tert.-butyl-3-hydroxy-2,6-dimethylbenzyl)-dithiolterephthalate, tris(3,5-ditert.-butyl-4-hydroxybenzyl)isocyanurate, the triester of beta-(4-hydroxy-3,5-ditert.-butyl-phenyl)propionic acid with 1,3,4-tris-(2-hydroyethyl)-5-triazin-2,4,6,(1H, 3H, 5H)-trione, bis-[3,3-bis-(4′-hydroxy-3-tert.-butylphenyl)-butyricacid]glycol ester, 1,3,5-trimethyl-2,4,6-tris-(3,5-ditert.-butyl-4-hydroxy-benzyl)benzene, 2,2′-methylene-bis-(4-methyl-6-tert.-butylphenyl)terephthalate, 4,4-methylene-bis-(2,6-di-tert.-butyl-phenol),4,4′-butylidene-bis-(tert.-butyl-metacresol), 2,2′-methylene-bis-(4-methyl-6-tert.-butyl)-phenol.

Sulphur-containing antioxidative co-stabilizers which may be used include for example distearylthiodipropionate, dilaurylthiodipropionate, methane tetrakis(-methylene-3-hexyl-thiopropionate), methane tetrakis(-methylene-3-dodecylthiopropionate) and dioctadecyl-disulphide. Phosphorus-containing co-stabilizers include for example trinonylphenyl phosphite, 4,9-distearyl-3,5,8,10-tetraoxadiphosphaspiroundecane, tris-(2,4-ditert.-butylphenyl)phosphite and tetrakis(2,3-ditert.-butylphenyl)-4,4′-bisphenylene diphosphonite. Further additives such as aminoaryl compounds and U.V.-absorbers and light stabilizers e.g. 2-(2′-hydroxyphenyl)-benzotriazoles, 2-hydroxybenzophenones, 1,3- bis-(2'-hydroxybenzoyl)benzene, salicylates, cinnamates, benzoates and substituted benzoates, sterically hindered amines and oxalic acid diamides may be used. Other known types of additives, e.g. flame retardants and antistatic agents may also be added.

The compounds of the invention can also be used in photopolymeric substrates containing photoinitiators for the photopolymerisation.

The compounds of formula I are especially suitable for use in organic polymer-containing coatings, particularly automotive finishes.

Automotive finishes are generally solutions or dispersions of organic polymers or polymer precursors in organic solvents. The majority are stoving finishes, which require the application of heat, generally above 80° C., in order to harden the finish in an acceptable time once it has been applied to the primer-coated metal surface. The hardening step may be accelerated by the use of an acid catalyst. The effect of this heating may be to accelerate the chemical reaction between polymer precursors in a thermosetting system, or to bring about fusion of particles of a thermoplastic polymer.

Many automotive finishes are metallic finishes, which contain flakes of metal, usually aluminium, in order to provide optical effects due to reflection. Such finishes are often two-coat finishes, in which a clear top coat finish is applied over a base coat finish containing a single pigment or metal flakes. The compounds of formula I can be in the top coat finish or the ground coat finish, preferably the former. Such two-coat metallic finishes have particular need of U.V.-stabilisers in the top coat, since the polymer in this coat is not protected by light-absorbing pigments, and it is subjected to almost double the normal amount of radiation because of reflection of light from the lower metallic layer.

The compounds of formula I are suitable for use as U.V.-stabilisers in a wide range of liquid finishes, for example those based on combinations of melamine-formaldehyde resins with oil-modified polyester resins, polyacrylate resins with added crosslinkers, or saturated polyesters; or on self-crosslinkers, or saturated polyesters; or on self-crosslinked polyacrylate or polyacrylate resin co-polymerised with styrene.

Further examples are two-component finishes based on an aliphatic or aromatic di-isocyanate and a hydroxy-group-containing polyacrylate, polyester or polyether resin. These polyurethane 2 component finishes are preferably hardened at 60° to 120° C. Thermoplastic polyacrylate resins may also be used, the latter being particularly useful in metallic finishes, as are also polyacrylate resins with added crosslinkers in combination with melamine-formaldehyde resins etherified with butanol and, further, hydroxy-group-containing polyacrylate resins hardened with aliphatic di-isocyanates. Such polyacrylate resins are described in U.S. Pat. No. 3,062,753, the contents of which are incorporated herein by reference.

The compounds of formula I are particularly useful in acid catalysed stoving finishes particularly in the top coat of two layer metallic finishes.

The compounds of formula I may be added to the finish at any stage in its manufacture, and may be added in solid form or in solution, preferably in the form of a liquid concentrate in a suitable solvent or in the form of a dispersion in water or organic solvent.

In practice, the compounds of formula I are added to a finish as a solution in organic solvent (as a liquid finish) in which the binder material is between 35% (low solid finishes) and 70% by weight (high solid finishes). The binder material of the finish can be in aqueous emulsion or suspension form (as an aqueous finish) in which the binder material part makes up 20 to 30% by weight. However, the compounds of formula I can be added to known powder finishes.

The compounds of formula I are to be added to the liquid or powder finishes before stoving or hardening. Preferably the compounds of formula I are used in liquid finishes since it is easy to add exact dosages. It is particularly preferred to use a concentrate (preferably in a hydrocarbon solvent) containing at least 40% preferably 60 to 80% by weight of the total weight of the concentrate of a compound of formula I to introduce the compound of formula I to finishes for stoving.

The addition of from 0.01 to 5% by weight, preferably 0.02 to 2% by weight of one or more compounds of formula I gives a clear improvement in the light- and weather-stability of organic pigments in stoving finishes as well as reducing the tendency to hairline cracking and loss of gloss as the result of weathering. This is also found for metallic finishes and excellent long-term stability of the clear top coat of two layer metallic finishes is obtained. In such finishes, the compound of formula I may be added to the metallic undercoat, the clear top coat or both, preferably only to the clear top coat. The metal surface to be finished may be under-coated with primer coatings as is customary in the art of coating metal surfaces.

The invention will now be illustrated by the following Examples in which all parts and percentages are by weight and all temperatures are in °C.

EXAMPLE 1

The preparation of the compound of formula 1a

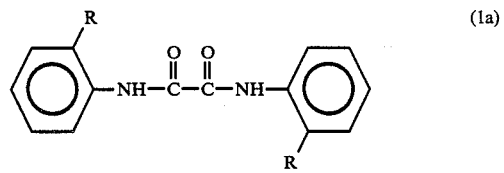

in which both groups R are

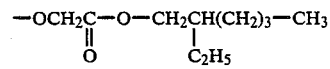

can be carried out as follows:

13.6 g of 2,2'-dihydroxyoxalanilide are dissolved at 60° to 62° in 150 ml of tetrahydrofurane. 24.8 g of potassium carbonate and 1.0 g of potassium iodide are added. To this suspension 21.7 g of chloroacetic acid-iso-octylester are added dropwise over 30 minutes and this mixture is stirred at this temperature until thin layer chromatography shows complete reaction has occurred. Water is then added and the upper organic phase is separated off and is then washed twice with water. The organic phase is then concentrated and the product is crystallized out of hexane. The product that results is a white powder having a melting point of 64° to 66°.

EXAMPLE 2

The preparation of the compound of formula 2a

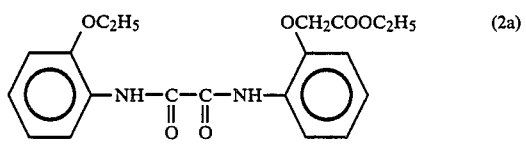

(2a)

EXAMPLES 3-7

The compounds detailed in the Table below can be prepared from suitable starting products by a method analogous to that of Example 1 or 2.

TABLE

| Ex. No. | Structure | m. point |
|---|---|---|
| 3 | $OC_2H_5$ / $O-CH_2-COOC_8H_{17}(i)$ | — |
| 4 | $H_5C_2-OOC-CH_2-O$ / $O-CH_2-COOC_2H_5$ | 169–170° C. |
| 5 | $(n)H_{17}C_8-OOC-CH_2-O$ / $O-CH_2-COO-C_8H_{17}(n)$ | — |
| 6 | $(n)H_9C_4-OOC-CH_2-O$ / $O-CH_2-COO-C_4H_9(n)$ | 117–118° C. |
| 7 | (bis-tetramethylpiperidine structure) | over 250° | can be carried out as follows:

15.0 g of 2-ethoxy-2'-hydroxyoxalanilide are added to 100 ml of acetone. 12.4 g of potassium carbonate and 1.0 g of potassium iodide are added and the mixture is warmed to 45°–50°.

At this temperature 6.1 g of chloroacetic acid ethyl ester are added and the mixture is stirred overnight. The suspension is filtered and the acetone solution is concentrated. The residue is crystallized out of toluene. The product is a white powder having a melting point of 115°–118°.

Alternatively, in Example 7 the N-unsubstituted 2,2,6,6-tetramethylpiperidine groups may be replaced by N-methyl-2,2,6,6-tetramethylpiperidine groups (Example 8) or by N-acetyl-2,2,6,6-tetramethylpiperidine groups (Example 9).

EXAMPLES 10-16

Compounds of the formula

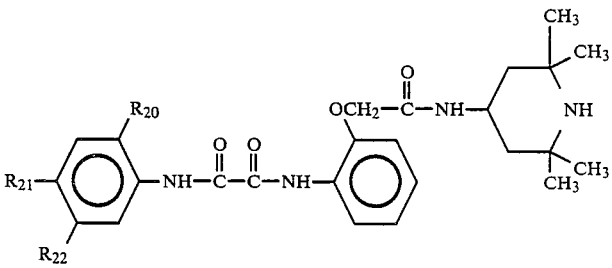

in which $R_{20}$ to $R_{22}$ are defined in the Table below can be prepared by a method analogous to that of Example 1 or 2 from suitable reactants.

TABLE

| Example No. | $R_{20}$ | $R_{21}$ | $R_{22}$ |
|---|---|---|---|
| 10 | —H | —H | —H |
| 11 | —C$_2$H$_5$ | —H | —H |
| 12 | —OCH$_3$ | —H | —H |
| 13 | —OCH$_3$ | —OCH$_3$ | —H |
| 14 | —H | —nC$_4$H$_9$ | —H |
| 15 | —CH$_3$ | —CH$_3$ | —H |
| 16 | —OCH$_3$ | —H | —CH$_3$ |

EXAMPLE 17

The compound of formula 17a

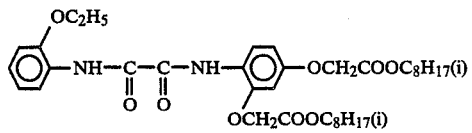

can be prepared by a method analogous to that of Example 1 by reacting 1 mole of 2-ethoxy-2',4'dihydroxyoxalanilide with 2 moles of chloroacetic acid isooctyl ester.

EXAMPLE 18

The compound of formula 18a

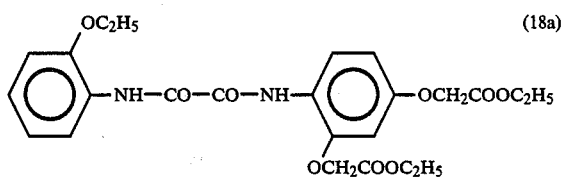

can be made by a method analogous to that of Example 17 from appropriate reactants.

EXAMPLE 19 AND 20

By a method analogous to that of Example 1 from appropriate reactants the compound of formula 19a or 20a

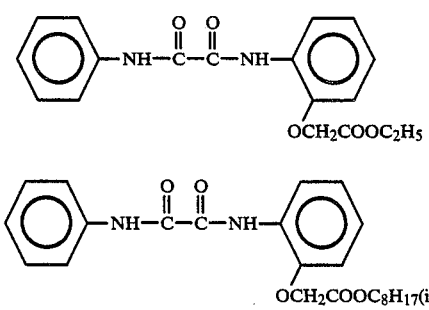

can be prepared.

APPLICATION EXAMPLE A

A clear finish of

| 80 Parts | of Viacryl SC 344 (a 50% solution of an acryl resin from Vianova), |
|---|---|
| 13.9 Parts | of Maprenal MF 80 (a 72% solution of a melamine resin from Hoechst) and |
| 4.1 Parts | of Byketol OK (from Byk-Malinckrodt) | is added to 2 parts of a compound of formula 1a (described in Example 1). After 1 minute the light stabiliser material so formed is dissolved in a finish. The finish is applied conventionally (according to the known 2 layer procedure) to a metallic or single pigment finish whilst still wet by spraying to form a layer having a thickness of 30 to 40 μm. The resulting coating is then hardened at 140° C. for 30 minutes. The coating shows very good resistance to U.V. light and weathering.

APPLICATION EXAMPLE B

A clear finish of

| 29.5 Parts | of Setalux C-1502 X-60 (a 60% solution of an acryl resin from Synthese B.V.), |
|---|---|
| 39.2 Parts | of Setalux C-1382 BX-45 (a 45% solution of an acryl resin from Synthese B.V.). |
| 21.4 Parts | of Setamine US-138 BB-70 (a 70% solution of a melamine resin from Synthese B.V.). |
| 2.5 Parts | of Baysilonoil [(2% solution in Xylene) from Bayer] and |
| 7.5 Parts | of Depanol Y (a solvent from Hoechst) | is stirred together with 2.5 parts of a compound of formula 1a (described in Example 1) and 2 parts of an acid catalyst derived from phosphoric acid (Type: Catalyst 296-9 from American Cyanamid) to form a homogeneous mixture. The finish is applied conventionally (according to the known 2 layer procedure) to a metallic or single pigment finish whilst both are still wet by spraying to form a layer having a thickness of 30 to 40 μm. The resulting coating is then hardened at 110° C. for 20 minutes. The coating shows very good resistance to U.V. light and weathering.

APPLICATION EXAMPLE C

A clear finish of

| 75 Parts | Macrynal SH 510 N (a hydroxy containing acryl resin from Bayer) |
|---|---|
| 2 Parts | of Baysilon-oil A [(1% solution in xylene) from Bayer] |
| 0.3 Parts | of dibutyl zinc dilaurate |
| 0.35 Parts | diethanolamine |
| 5.0 Parts | of ethylglycol acetate |
| 5.0 Parts | of Solvesso 100 |
| 6.0 Parts | of Xylene and |
| 6.35 Parts | of butyl acetate | is added to 23.5 parts of a compound of formula 1a (described in Example 1) and 30 parts of Desmodur N 75 (from Bayer). The homogeneous mixture so formed is applied conventionally (according to the known 2 layer procedure) to a metallic or single pigment finish whilst both are still wet by spraying to form a layer having a thickness of 30 to 40 μm and the resulting coating is hardened over 20 minutes at 80° to 90° C. The resulting 2K-PUR coating shows a good resistance to U.V. light and weathering.

APPLICATION EXAMPLE D

A single white pigmented finish of

| | |
|---|---|
| 14.30 Parts | of Setamine US-132 BB 70 (a 70% solution of a melamine resin from Synthese) |
| 57.15 Parts | of Setal 84 W-70 (a 70% solution of an alkyd resin from Synthese) |
| 7.70 Parts | of n-butanol |
| 1.85 Parts | of butylglycol acetate |
| 9.50 Parts | of xylene and |
| 25 Parts | of titanium dioxide (Rutil type) | is added with 1.38 parts of the product of formula Ia (see Example 1). The finish is conventionally applied to a grounded steel metal to which a filler having a layer thickness 20 to 30 μm has been annealed;, by spraying and after standing for 30 minutes at room temperature the steel metal surface is annealed at 120° C. for 30 minutes. The resulting coating shows very good resistance to U.V. light and weathering.

In Application Examples A to D instead of the product of formula Ia, an appropriate amount of the product of anyone of Examples 2 to 20 can be used.

For the avoidance of doubt in the above Application Examples appropriate amounts of one or more of the products of Examples 2 to 20 can be used in place of the compound of formula I.

What is claimed is:

1. A compound of formula I

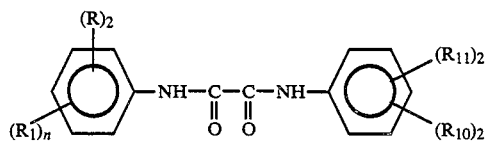

in which each R independently, is hydrogen, $C_{1-8}$alkyl, $C_{1-8}$alkoxy or halogen or both groups R are attached to carbon atoms in a position ortho to one another and together with the carbon atoms to which they are attached form a cyclopentylene or cyclohexylene group;

n is 1 or 2;

$R_1$ is $-OCH_2-CO-X-R_4$ where X is $-O-$ or $-N(R_3)-$;

$R_4$ is

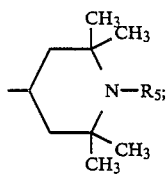

$R_3$ is hydrogen or $C_{1-4}$alkyl; and $R_5$ is hydrogen, oxygen, $C_{1-8}$alkyl or $-CO-R_6$;

$R_6$ is $C_{1-6}$alkyl, phenyl, $-CO-OC_{1-4}$alkyl or $-NR_7R_8$;

$R_7$ is hydrogen, $C_{1-12}$alkyl; $C_{5-6}$cycloalkyl, phenyl or $C_{1-12}$alkyl phenyl;

$R_8$ is hydrogen or $C_{1-12}$alkyl;

each $R_{10}$ independently is selected from hydrogen, halogen $C_{1-4}$alkyl, $C_{2-4}$alkenyl, $C_{1-8}$alkoxy, phenoxy, phenyl, phenyl$C_{1-4}$alkyl or $C_{1-4}$alkyl phenyl; and each $R_{11}$ independently is a significance of $R_{10}$ or $R_1$; or both groups $R_{11}$ are hydrogen and both groups $R_{10}$ are attached to carbon atoms ortho to one another and together with the carbon atoms to which they are attached form a carbocyclic or heterocyclic group.

2. A comound according to claim 1, in which R is R' where R' is hydrogen or $C_{1-4}$alkoxy.

3. A compound according to claim 1, in which $R_1$ is $R_1'$ where $R_1'$ is $-O-CH_2COR_4'$ where $R_4'$ is N-unsubstituted, N-methyl or N-acetyl-2,2,6,6-tetramethylpiperidinyl.

4. A compound according to claim 1 of formula II or III

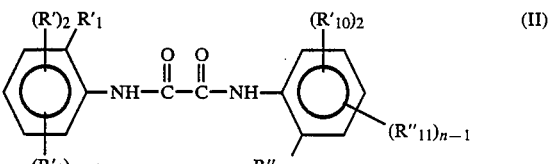

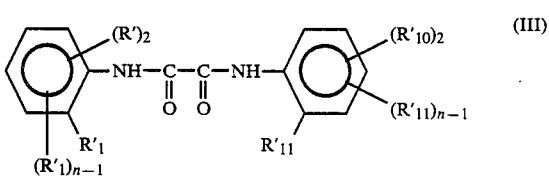

in which

R' is hydrogen or $C_{1-4}$alkoxy;

$R_1'$ is $-O-CH_2COOR_4'$, where $R_4'$ is N-unsubstituted, N-methyl or N-acetyl 2,2,6,6-tetramethyl piperidinyl;

$R_{10}'$ is hydrogen, chloro, $C_{1-4}$alkyl, $C_{1-4}$alkoxy, phenyl or phenoxy;

$R_{11}'$ is a significance of $R_1'$ or $R_{10}'$ independently of $R_1'$ or $R_{10}'$;

$R_{11}''$ is a significance of $R_1'$ independently of $R_1'$.

5. A compound according to claim 1 of the formula

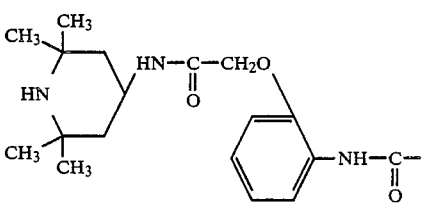

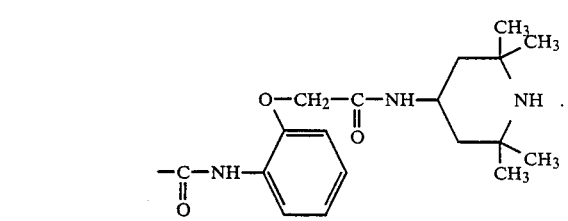

6. A compound of the formula

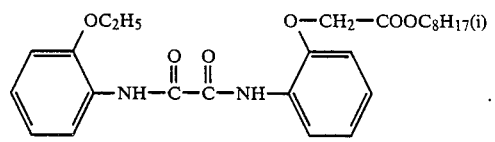

7. A compound of formula II

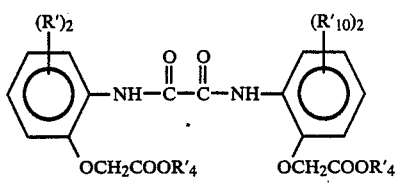

(II)

in which each R' is hydrogen or $C_{1-4}$ alkoxy;

each $R_4'$, independently, is linear or branched $C_{4-12}$alkyl or N-unsubstituted, N-methyl or N-acetyl 2,2,6,6-tetramethylpiperidinyl; and $R_{10}'$ is hydrogen, chloro, $C_{1-4}$alkyl, $C_{1-4}$alkoxy, phenyl or phenoxy.

8. A compound according to claim 7 of formula 1a

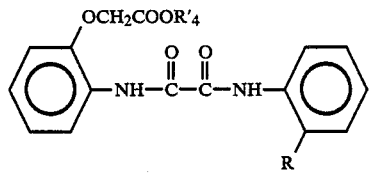
(1a)

in which both groups $R_4'$ are

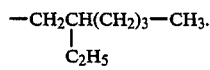

9. A compound according to claim 7 of the formula

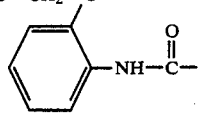

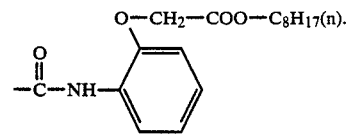

10. A compound according to claim 7 of the formula

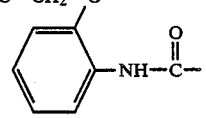

11. A substrate to which a compound of formula I, defined in claim 1, has been applied.

12. A lacquer composition comprising a polymeric material selected from the group consisting of acrylic, alkyd and polyester resins and a compound according to claim 1 in an amount sufficient to protect the polymeric material against degradation by light.

13. A lacquer composition comprising a polymeric material selected from the group consisting of acrylic, alkyd and polyester resins and a compound according to claim 7 in an amount sufficient to protect the polymeric material against degradation by light.

* * * * *